United States Patent
Hiruma et al.

(10) Patent No.: US 11,234,916 B2
(45) Date of Patent: Feb. 1, 2022

(54) HAIR COSMETIC

(71) Applicant: KAO CORPORATION, Tokyo (JP)

(72) Inventors: Daisuke Hiruma, Kurfuerstenstrasse (DE); Tomoyuki Suzawa, Kawasaki (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/961,808

(22) PCT Filed: Jan. 16, 2019

(86) PCT No.: PCT/JP2019/001061
§ 371 (c)(1),
(2) Date: Jul. 13, 2020

(87) PCT Pub. No.: WO2019/142815
PCT Pub. Date: Jul. 25, 2019

(65) Prior Publication Data
US 2021/0069081 A1 Mar. 11, 2021

(30) Foreign Application Priority Data
Jan. 16, 2018 (JP) .............................. JP2018-005199

(51) Int. Cl.
| | | |
|---|---|---|
| A61Q 5/00 | (2006.01) |
| A61K 8/46 | (2006.01) |
| A61K 8/19 | (2006.01) |
| A61K 8/22 | (2006.01) |
| A61K 8/23 | (2006.01) |
| A61K 8/31 | (2006.01) |
| A61K 8/33 | (2006.01) |
| A61K 8/34 | (2006.01) |
| A61K 8/41 | (2006.01) |
| A61K 8/42 | (2006.01) |
| A61K 8/49 | (2006.01) |
| A61K 8/55 | (2006.01) |
| A61K 8/92 | (2006.01) |
| A61Q 5/08 | (2006.01) |
| A61Q 5/10 | (2006.01) |

(52) U.S. Cl.
CPC ............... *A61K 8/466* (2013.01); *A61K 8/19* (2013.01); *A61K 8/22* (2013.01); *A61K 8/23* (2013.01); *A61K 8/31* (2013.01); *A61K 8/33* (2013.01); *A61K 8/342* (2013.01); *A61K 8/345* (2013.01); *A61K 8/347* (2013.01); *A61K 8/41* (2013.01); *A61K 8/415* (2013.01); *A61K 8/416* (2013.01); *A61K 8/42* (2013.01); *A61K 8/4913* (2013.01); *A61K 8/4926* (2013.01); *A61K 8/4973* (2013.01); *A61K 8/55* (2013.01); *A61K 8/925* (2013.01); *A61Q 5/08* (2013.01); *A61Q 5/10* (2013.01)

(58) Field of Classification Search
CPC ... A61Q 5/06; A61Q 5/10; A61Q 5/12; A61K 2800/594; A61K 2800/5426; A61K 8/898; C08G 77/452; A45D 7/06
USPC ......................................................... 424/70.1
See application file for complete search history.

(56) References Cited

U.S. PATENT DOCUMENTS

| | | | |
|---|---|---|---|
| 5,683,685 A | 11/1997 | Hirano et al. | |
| 2010/0229314 A1* | 9/2010 | Takiguchi | A61Q 5/10 8/405 |
| 2011/0150804 A1* | 6/2011 | Nojiri | A61K 8/365 424/70.1 |
| 2016/0120783 A1* | 5/2016 | Horie | A61K 8/732 424/62 |

FOREIGN PATENT DOCUMENTS

| | | | |
|---|---|---|---|
| JP | 8-198732 | A | 8/1996 |
| JP | 2009-108052 | A | 5/2009 |
| JP | 2010-65022 | A | 3/2010 |
| JP | 2010-248123 | A | 11/2010 |
| JP | 2011-157312 | A | 8/2011 |
| JP | 2015-13855 | A | 1/2015 |
| JP | 2016-104706 | A | 6/2016 |

OTHER PUBLICATIONS

STIC Search Report dated May 10, 2021.*
International Search Report dated Feb. 26, 2019 in PCT/JP2019/001061 filed on Jan. 16, 2019, 2 pages.

* cited by examiner

*Primary Examiner* — Eisa B Elhilo
(74) *Attorney, Agent, or Firm* — Oblon, McClelland, Maier & Neustadt, L.L.P.

(57) ABSTRACT

A hair cosmetic comprising the following components (A) and (B) at a mass ratio of component (B) to component (A), (B)/(A), of 0.7 or more and 5.0 or less:
(A) an aromatic sulfonic acid having a molecular weight of 300 or less or a salt thereof; and
(B) a cationic polymer having a cationic charge density of 4.5 meq/g or more.

30 Claims, No Drawings

HAIR COSMETIC

FIELD OF THE INVENTION

The present invention relates to a hair cosmetic.

BACKGROUND OF THE INVENTION

It is known that hair is damaged by chemical treatments such as hair coloration and permanent waves, resulting in deterioration of the feel, such as stiff handfeel. Especially in the thick hair peculiar to the Asian people, this deterioration of the feel is noticeably observed. Furthermore, damaged hair is affected by behaviors such as daily hair washing and drying by a dryer, and the denaturation, swelling, and outflow of proteins in the hair are apt to proceed. As a result, frizzy hair and hair swelling are strongly developed, and it leads to deteriorated hair feel, such as hair spreading, irregular hair shape, and dry hair and tangled hair caused by them. In addition, deterioration of hair alignment and deterioration of the hair manageability accompanied by these remind users of feel even more damaged feeling.

The hair cosmetics currently mainly used for reducing the influence of the above-mentioned damage include emulsion products such as a hair cream-type containing a wax, a higher alcohol, a surfactant and the like, or gel products containing a film-forming polymer (setting polymer) in order to impart hair manageability and prevent drying from hair. However, although such hair cosmetics can temporarily solve problems such as poor hair manageability and dryness by attaching oils/fats and polymers to the hair surface, they have not been able to substantially improve the hair luster and hair manageability.

Meanwhile, it is known that a hair cosmetic containing a specific organic acid, a specific organic solvent, and a specific di- or tri-peptide are excellent in the effect of imparting hair manageability and good hair feel, and preventing hair dryness (see Patent Literature 1).

It is also known that a hair treatment composition containing an organic solvent, a specific aromatic sulfonic acid, a certain surfactant, and an oil agent can impart firmness/strength and a conditioning effect to hair (see Patent Literature 2).

CITATIONS

Patent Literature 1: JP 2011-157312A
Patent Literature 2: JP hei 08-198732A

SUMMARY OF THE INVENTION

The present invention provides a hair cosmetic comprising the following components (A) and (B), wherein a mass ratio of (B) to (A), (B)/(A), is 0.7 or more and 5.0 or less.

(A) an aromatic sulfonic acid having a molecular weight of 300 or less or a salt thereof
(B) a cationic polymer having a cationic charge density of 4.5 meq/g or more The present invention also provides a hair bleaching or hair dyeing kit composed of the hair cosmetic and a hair bleaching agent or an oxidative hair dyeing agent comprising a first agent comprising an alkaline agent and a second agent comprising an oxidizing agent.

The present invention further provides use of the hair cosmetic as a pretreatment agent for a hair bleaching agent or an oxidative hair dyeing agent comprising a first agent comprising an alkaline agent and a second agent comprising an oxidizing agent.

The present invention further provides a hair bleaching or hair dyeing process comprising the following steps (i) and (ii):

(i) a step of applying the hair cosmetic to hair;
(ii) a step of applying a solution mixture of a first agent comprising an alkaline agent and a second agent comprising an oxidizing agent of the hair bleaching agent or an oxidative dyeing agent to the hair after the step (i).

Advantageous Effect of the Invention

The hair cosmetic of the present invention provides an excellent hair-modifying effect of suppressing the hair swelling and hair spreading which occur naturally or after a chemical treatment such as hair dyeing, and of sustaining the hair manageability effect for a certain period of time, with a single treatment.

DETAILED DESCRIPTION OF THE INVENTION

The hair cosmetic described in the Patent Literature 1 exhibits excellent hair modifying effects, and is effective in imparting hair manageability and good hair feel, preventing hair dryness, and further improving the uniformed hair tip direction and the hair smoothness. However, if the hair cosmetic is rinsed off by washing treatment such as shampooing, the effect of the hair cosmetic can be attenuated. Hence the hair cosmetic does not exert a prolonged hair manageability effect. The hair treatment compositions described in the Patent Literature 2 can impart firmness, strength, smoothness to the hair, but do not improve the manageability impaired by hair damage.

Moreover, the levels of hair-modifying effects sought by the recent users are getting higher and higher year by year. In addition, due to changes in the social and living environment, the recent users have less spare time. As such, there is a need to obtain a long-lasting effect in fewer steps. Under the circumstances, recently, conventional hair cosmetics have not been sufficient to adequately meet the requirements of such users.

Accordingly, the present invention relates to a hair cosmetic providing an excellent hair-modifying effect of suppressing the hair swelling and hair spreading which occur naturally or after a chemical treatment such as hair dyeing, and of sustaining the hair manageability effect for a certain period of time, with a single treatment.

The present inventors found that by a hair cosmetic employing a combination of an aromatic sulfonic acid with a cationic polymer having specific charge-densities at a certain ratio provides high hair modifying effects satisfying the above requirements, thereby completing the present invention.

[Component (A): Aromatic Sulfonic Acid Having Molecular Weight of 300 or Less or Salt Thereof]

Examples of the aromatic sulfonic acid having a molecular weight of 300 or less or a salt thereof as component (A) include benzenesulfonic acids, naphthalenesulfonic acids, azulenesulfonic acids, and benzophenonesulfonic acids.

Examples of the benzenesulfonic acids include compounds represented by the following formula (1):

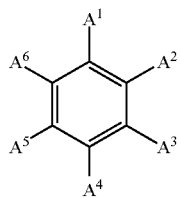

(1)

where at least one of $A^1$ to $A^6$ represents a sulfo group or a salt thereof, and the remainder are each a hydrogen atom or a C1-C3 alkyl group.

Examples of the benzenesulfonic acids include benzenesulfonic acid, o-toluenesulfonic acid, p-toluenesulfonic acid, xylenesulfonic acid, cumenesulfonic acid, ethylbenzenesulfonic acid, and 2,4,6-trimethylbenzenesulfonic acid, and a salt thereof.

Examples of the naphthalenesulfonic acids include compounds represented by the following formula (2):

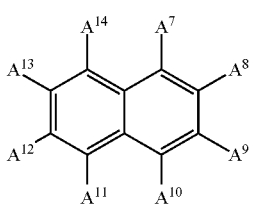

(2)

where at least one of $A^7$ to $A^{14}$ represents a sulfo group or a salt thereof, and the remainder are each a hydrogen atom, a halogen atom, a hydroxy group, a nitro group, a carboxy group, a C2-C4 alkoxycarbonyl group, a C1-C3 alkyl group, a C1-C3 alkoxy group, a formyl group, a C2-C3 alkenyl group, a C2-C3 acyl group, an optionally substituted phenylazo group, or —N(R')(R'') (R' and R'' each represent a hydrogen atom, a C1-C3 alkyl group, a C2-C3 alkenyl group, a phenyl group, a benzyl group, or a C2-C3 acyl group).

Examples of the naphthalenesulfonic acids include 1- or 2-naphthalenesulfonic acid (α- or β-naphthalenesulfonic acid), 2,7-naphthalenedisulfonic acid, 1,5-naphthalenedisulfonic acid, 2,6-naphthalenedisulfonic acid, 1-naphthol-2-sulfonic acid, 1-naphthol-4-sulfonic acid, 2-naphthol-6-sulfonic acid, 2-naphthol-7-sulfonic acid, 2,3-dihydroxynaphthalene-6-sulfonic acid, 1,7-dihydroxynaphthalene-3-sulfonic acid, J acid (2-amino-5-naphthol-7-sulfonic acid), 1-amino-2-naphthol-4-sulfonic acid, 1-naphthylamine-4-sulfonic acid, Bronner's acid (2-naphthylamine-6-sulfonic acid), Cleve's acid (1-naphthylamine-7-sulfonic acid), 2-naphthylamine-1-sulfonic acid, l-naphthylamine-6-sulfonic acid, l-naphthylamine-8-sulfonic acid, 2,7-diamino-1-naphthol-3-sulfonic acid, 7,8-diamino-1-naphthol-3-sulfonic acid, naphthalenesulfonic acid-formalin polycondensates having a molecular weight of 300 or less, 6-methyl-2-naphthalenesulfonic acid, 4-ethyl-1-naphthalenesulfonic acid, 5-isopropyl-1-naphthalenesulfonic acid, and 5-butyl-2-naphthalenesulfonic acid, and a salt thereof.

Examples of the azulenesulfonic acids include guaiazulenesulfonic acid, 1-azulenesulfonic acid, 3-acetyl-7-isopropyl-1-azulenesulfonic acid, 3-(2-hydroxyethyl)-7-isopropyl-1-azulenesulfonic acid, 3-methyl-7-isopropyl-1-azulenesulfonic acid, 7-isopropyl-1-azulenesulfonic acid, 1,4-dimethyl-7-isopropyl-2-azulenesulfonic acid, 1,3-azulenedisulfonic acid, and 3-formyl-4,6,8-trimethyl-1-azulenesulfonic acid, and a salt thereof.

Examples of the benzophenonesulfonic acids include compounds represented by the following formula (3):

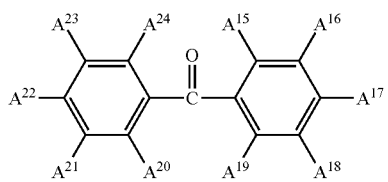

(3)

where at least one of $A^{15}$ to $A^{24}$ represents a sulfo group or a salt thereof, and the remainder are each a hydrogen atom, a halogen atom, a hydroxy group, a carboxy group, an amino group, a C1-C3 alkyl group, a C1-C3 alkoxy group, a C2-C3 alkenyl group, or a C2-C3 acyl group.

Examples of the benzophenonesulfonic acids include an o-chlorobenzophenonesulfonic acid, p-chlorobenzophenonesulfonic acid, 2-hydroxybenzophenonesulfonic acid, 4-hydroxybenzophenonesulfonic acid, 2-aminobenzophenonesulfonic acid, 4-aminobenzophenonesulfonic acid, 2-methylbenzophenonesulfonic acid, 4-methoxybenzophenonesulfonic acid, and 4,4'-dimethylbenzophenonesulfonic acid, and a salt thereof.

Examples of the salts of the above-mentioned aromatic sulfonic acids include a sodium salt, a potassium salt, a lithium salt, an aluminum salt, an ammonium salt ($NH^{4+}$), and an organic ammonium salt.

The aromatic sulfonic acid or a salt thereof as component (A) is preferably at least one selected from the group consisting of benzenesulfonic acids represented by formula (1), naphthalenesulfonic acids represented by formula (2), and benzophenonesulfonic acids represented by formula (3) and further preferably at least one selected from the group consisting of p-toluenesulfonic acid, xylenesulfonic acid, 2-naphthalenesulfonic acid (β-naphthalenesulfonic acid), and 1-naphthalenesulfonic acid (α-naphthalenesulfonic acid), and a salt thereof, from the viewpoint of, when combined with component (B) at a specific ratio, mitigating the hair swelling, improving the hair manageability, mitigating further strongly the frizzy hair, giving a soft feel to the hair, and preventing the hair from being tangled. In particular, p-toluenesulfonic acid or a salt thereof is further preferred from the above-mentioned viewpoint.

These aromatic sulfonic acids or salts thereof can be used alone or in combination of two or more thereof. The content of component (A) in the hair cosmetic of the present invention is preferably 0.01 mass % or more, more preferably 0.05 mass % or more, further preferably 0.10 mass % or more, further preferably 0.20 mass % or more, further preferably 0.30 mass % or more, further preferably 0.50 mass % or more, further preferably 0.80 mass % or more, and further preferably 0.9 mass % or more from the viewpoint of, mitigating the hair swelling and improving the hair manageability when combined with component (B) at a specific ratio, and is preferably 5 mass % or less, more preferably 3.0 mass % or less, further preferably 2.0 mass % or less, further preferably 1.5 mass % or less, and further preferably 1.2 mass % or less from the viewpoint of suppressing the chronological change in viscosity which may be caused by a decrease in pH.

[Component (B): Cationic Polymer Having Cationic Charge Density of 4.5 meq/g or More]

Examples of the cationic polymer having a cationic charge density of 4.5 meq/g or more as component (B) include dimethyldiallylammonium chloride polymers (Polyquaternium-6, for example, Merquat 100 (charge density: 6.18 meq/g), Lubrizol Advanced Materials, Inc.), dimethyldiallylammonium chloride-acrylic acid copolymers (Polyquaternium-22, for example, Merquat 280 (charge density: 4.99 meq/g) and Merquat 295 (charge density: 6.05 meq/g), Lubrizol Advanced Materials, Inc.), polyethylene imines (Epomin P-1000 (charge density: 18 meq/g), Nippon Shokubai Co., Ltd.), copolymers of vinylpyrrolidone and methylvinylimidazolium chloride (Luviquat Excellence (charge density: 6.7 meq/g), manufactured by BASF), and polymers of methacryloyloxyethylene trimonium chloride (Polyquaternium-37, for example, Cosmedia Ultragel 300 (charge density: 4.8 meq/g), BASF). In particular, a cationic polymer including a dimethyl diallyl quaternary ammonium salt monomer is preferred from the viewpoint of mitigating the hair swelling and improving the hair manageability when combined with component (A) at a specific ratio, and the cationic polymer more preferably has a molar fraction of the monomer of 70% or more, further preferably 80% or more, and further more preferably 90° or more.

The cationic charge density of the cationic polymer as component (B) is preferably 4.8 meq/g or more, more preferably 5.0 meq/g or more, further preferably 5.6 meq/g or more, and further preferably 6.0 meq/g or more from the viewpoint of mitigating the hair swelling and improving the hair manageability when combined with component (A) at a specific ratio and is preferably 25 meq/g or less, more preferably 20 meq/g or less, further preferably 15 meq/g or less, further preferably 7.0 meq/g or less, further preferably 6.5 meq/g or less, and further preferably 6.2 meq/g or less from the viewpoint of improving the stability of the composition.

The cationic polymers as component (B) can be used alone or in combination of two or more thereof, and the content in the hair cosmetic of the present invention is preferably 0.1 mass % or more, more preferably 0.2 mass % or more, further preferably 0.25 mass % or more, further preferably 0.3 mass % or more, further preferably 0.5 mass % or more, further preferably 1.0 mass % or more, further preferably 1.5 mass % or more, and further preferably 1.7 mass % or more from the viewpoint of mitigating the hair swelling and improving the hair manageability when combined with component (A) at a specific ratio, and is preferably 20 mass % or less, more preferably 10 mass % or less, further preferably 8 mass % or less, further preferably 5 mass % or less, further preferably 3 mass % or less, further preferably 2.5 mass % or less, and further preferably 2.3 mass % or less from the viewpoint of suppressing the stickiness of the hair after finishing and improving the stability of the composition.

In addition, the mass ratio of component (B) to component (A), (B)/(A), is 0.7 or more, preferably 0.8 or more, more preferably 0.9 or more, further preferably 1.0 or more, further preferably 1.2 or more, further preferably 1.5 or more, and further preferably 1.7 or more and 5.0 or less, preferably 4.5 or less, more preferably 3.5 or less, further preferably 3.0 or less, further preferably 2.5 or less, and further preferably 2.3 or less from the viewpoint of mitigating the hair swelling and improving the hair manageability. It was found that when component (A) and component (B) are mixed within the range of the above-mentioned mass ratio, an adhesive, soft, and tough coating film can be formed. It follows that it can be considered that the coating film having the above-described physical properties can be formed on the hair surface by applying a hair cosmetic containing component (A) and component (B) in the above-mentioned mass ratio range to the hair and exhibits the effects of mitigating the hair swelling and improving the hair manageability by interaction between hairs. In addition, when the cationic charge density of component (B) is 4.5 meq/g or more, the adhesiveness of the coating film to the hair surface is enhanced, and the coating film is not easily washed off by a detergent to exhibit persistence of the hair-managing effect.

[Component (C): Glycylglycine Derivative Represented by Formula (4) or Salt Thereof]

The hair cosmetic of the present invention preferably further contains a compound represented by formula (4) or a salt thereof as component (C),

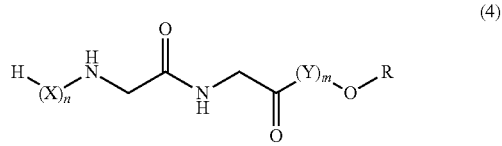

(4)

wherein X represents a divalent C1-C4 hydrocarbon group optionally substituted with a hydroxy group or an amino acid residue; Y represents an amino acid residue or a divalent group represented by the following chemical formula (5):

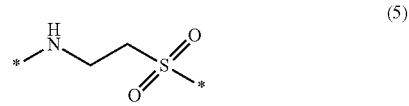 [SMILES: *NCCS(*)(=O)=O]

(5)

(wherein -* represents a bond that binds to an adjacent carbonyl group or oxygen atom); R represents a hydrogen atom or a monovalent C1-C4 hydrocarbon group optionally substituted with a hydroxy group; and m and n each represent 0 or 1 provided that when m and n are both 1, X is not an amino acid residue.

Component (C) is a glycylglycine derivative represented by formula (4) or a salt thereof and may be in a free form or an amphoteric ion. Examples of the salt of the glycylglycine derivative include an inorganic acid salt, such as hydrochloride and sulfate; an organic acid salt, such as lactate; an ammonium salt, such as an ammonium salt and an alkylammonium salt; and an alkali metal salt, such as a sodium salt.

In formula (4), the divalent C1-C4 hydrocarbon group optionally substituted with a hydroxy group represented by X may be saturated or unsaturated and may be linear or branched and is, among them, preferably a divalent saturated hydrocarbon group substituted with a hydroxy group or a divalent saturated hydrocarbon group.

Examples of the divalent hydrocarbon group include a methylene group, an ethylene group, an ethylidene group, a vinylene group, a trimethylene group, an isopropylidene group, a 1-propenylene group, a tetramethylene group, a 2-methyltrimethylene group, a 1-methyltrimethylene group, and 1-butenylene group.

Examples of the divalent hydrocarbon group substituted with a hydroxy group include a 1-hydroxyethylene group, a 1-hydroxytrimethylene group, a 1,2-dihydroxytrimethylene group, a 1-hydroxytetramethylene group, a 1,2-dihydroxytetramethylene group, a 1,3-dihydroxytetramethylene group, and a 1,2,3-trihydroxytetramethylene group.

In formula (4), the "amino acid residue" represented by X means a unit amino acid moiety derived from every amino acid synthesized or present in the body to be formed into an oligopeptide and it may be a D-form or an L-form.

Examples of the amino acid residue represented by X include basic amino acid residues, such as an arginine residue, a lysine residue, and a histidine residue; aliphatic amino acid residues, such as an alanine residue and a glycine residue; aromatic amino acid residues, such as a phenylalanine residue, a tyrosine residue, and a tryptophan residue; acid amide amino acid residues, such as a glutamine residue and an asparagine residue; acidic amino acid residues, such as a glutamic acid residue, an aspartic acid residue, and a cysteic acid residue; hydroxyamino acid residues, such as a serine residue and a threonine residue; and cyclic amino acid residues, such as a proline residue, an N-methylproline residue, and a 4-hydroxyproline residue. In particular, preferred are an arginine residue, an alanine residue, a phenylalanine residue, a glycine residue, a glutamine residue, a glutamic acid residue, a serine residue, a praline residue, an N-methylproline residue, and a 4-hydroxyproline residue.

In formula (4), examples of the amino acid residue represented by Y are the same as those exemplified in X, and Y is preferably an arginine residue, an alanine residue, a glycine residue, a glutamine residue, a glutamic acid residue, a serine residue, a proline residue, a 4-hydroxyproline residue, or a divalent group represented by chemical formula (5).

In formula (4), the monovalent C1-C4 hydrocarbon group optionally substituted with a hydroxy group represented by R may be saturated or unsaturated and may be linear or branched. The monovalent hydrocarbon group is preferably an alkyl group, and examples thereof include a methyl group, an ethyl group, a propyl group, a butyl group, an isopropyl group, an isobutyl group, an s-butyl group, and a t-butyl group.

The monovalent hydrocarbon group substituted with a hydroxy group is preferably a hydroxyalkyl group, and examples thereof include a hydroxymethyl group, a 2-hydroxyethyl group, a 3-hydroxypropyl group, a 4-hydroxybutyl group, a 2,3-dihydroxyethyl group, a 2,3,4-trihydroxybutyl group, and a 2,4-dihydroxybutyl group.

Examples of the glycylglycine derivative in the present invention include compounds represented by any one of formulae (G1) to (G10), more preferably compounds represented by any one of formulae (G3) to (G10) from the viewpoint of mitigating the hair swelling and improving the hair manageability, and particularly preferably compounds (glycylglycylglycine and glycylglycine) represented by formula (G9) or (G10). These glycylglycine derivatives may be in free forms or amphoteric ions and may form salts. In addition, they may be used alone or in combination of two or more thereof.

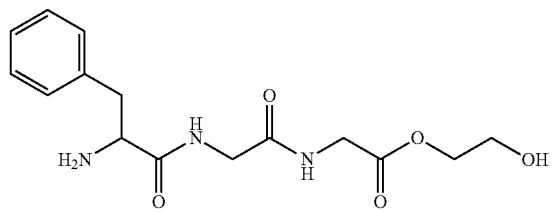
(G1)

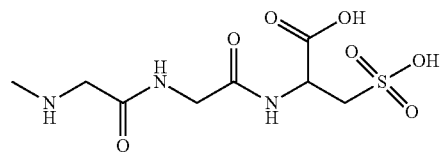
(G2)

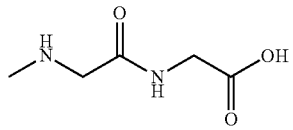
(G3)

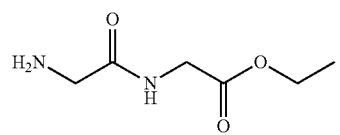
(G4)

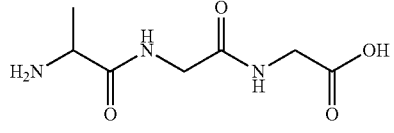
(G5)

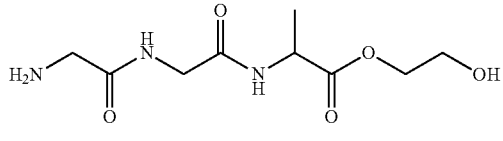
(G6)

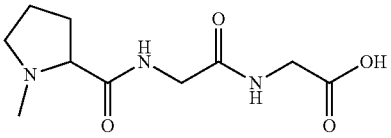
(G7)

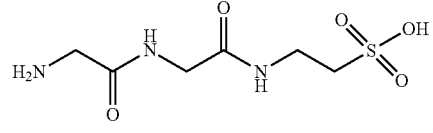
(G8)

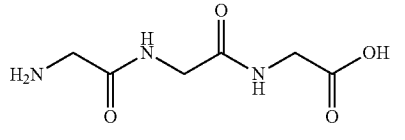
(G9)

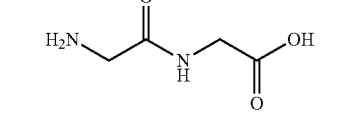
(G10)

The content of component (C) in the hair cosmetic of the present invention is preferably 0.01 mass % or more, more preferably 0.05 mass % or more, further preferably 0.1 mass % or more, further preferably 0.3 mass % or more, and further preferably 0.5 mass % or more from the viewpoint of mitigating the hair swelling and improving the hair manageability and from the viewpoint of suppressing the chronological change in viscosity when a thickener that is influenced by pH due to its pH buffering ability is used, and is preferably 10.0 mass % or less, more preferably 5.0 mass % or less, further preferably 3.0 mass % or less, further preferably 1.5 mass % or less, further preferably 1.2 mass % or less, and further preferably 1.0 mass % or less from the viewpoint of reducing the cost and preventing the adjustment of pH from becoming difficult due to the pH buffering ability.

The mass ratio of component (C) to the total mass of components (A) and (B) in the hair cosmetic of the present invention is preferably 0.1 or more, more preferably 0.2 or more, further preferably 0.3 or more, and further preferably 0.4 or more from the viewpoint of mitigating the hair swelling and improving the hair manageability and is preferably 5 or less, more preferably 4 or less, further preferably 3 or less, further preferably 2 or less, and further preferably 1 or less from the viewpoint of reducing the cost and preventing the adjustment of pH from becoming difficult due to the pH buffering ability.

[Medium]

The hair cosmetic of the present invention can contain water and/or an organic solvent as a medium and preferably contains water from the viewpoint of solubility of other components and economic efficiency. Examples of the organic solvent include a lower alkanol such as ethanol, 1-propanol, and 2-propanol; an aromatic alcohol such as benzylalcohol and 2-benzyloxyethanol; a polyol such as ethylene glycol, diethylene glycol, triethylene glycol, polyethylene glycol, propylene glycol, dipropylene glycol, polypropylene glycol, 1,2-butylene glycol, 1,3-butylene glycol, 1,4-butylene glycol, pentylene glycol, hexylene glycol, glycerol, diglycerol, and polyglycerol; an alkoxy alcohol such as ethoxyethanol, ethoxy diglycol, and methoxyethanol; an N-alkyl pyrrolidone such as N-methyl pyrrolidone and N-ethyl pyrrolidone; an alkylene carbonate such as propylene carbonate; and a lactone such as γ-valerolactone and γ-caprolactone. In addition, from the viewpoint of chronological viscosity stability, preferred are one or more selected from the group consisting of ethanol, propylene glycol, 1-propanol, 2-propanol, benzylalcohol, polyethylene glycol, and glycerol, and in particular, more preferred are one or two selected from the group consisting of ethanol and propylene glycol.

The content of water in the hair cosmetic of the present invention is preferably 45 mass % or more, more preferably 50 mass % or more, and further preferably 60 mass % or more from the viewpoint of solubility of other components and economic efficiency, and is preferably 99 mass % or less, more preferably 95 mass % or less, and further preferably 90 mass % or less from the viewpoint of the drying ability.

The organic solvents can be used alone or in combination of two or more thereof. The content of the organic solvent in the hair cosmetic of the present invention is preferably 0.05 mass % or more, more preferably 0.1 mass % or more, further preferably 0.5 mass % or more, further preferably 1 mass % or more, further preferably 3 mass % or more, and further preferably 5 mass % or more from the viewpoint of improving the solubility of other components, antiseptic properties, and viscosity stability, and is preferably 30 mass % or less, more preferably 20 mass % or less, and further preferably 10 mass % or less from the viewpoint of reducing the flammability and irritation.

[Thickener]

The hair cosmetic of the present invention can further contain a synthetic polymer compound, a semisynthetic polymer compound, or a natural polymer compound as a thickener from the viewpoint of adjusting the viscosity such that it can be uniformly applied to the hair of head and can be prevented from dripping. Examples of the synthetic polymer compound, the semisynthetic polymer compound, and the natural polymer compound include polyacrylic acids (e.g., Carbopol series 941 and 981; Lubrizol Advanced Materials, Inc.), acrylic acid-alkyl methacrylate copolymers (e.g., Carbopol ETD2020; Lubrizol Advanced Materials, Inc.), vinylpyrrolidone-dimethylaminoethyl methacrylate copolymers (e.g., Copolymer 845, Copolymer 937, and Copolymer 958; ISP Japan), methyl cellulose (e.g., Metolose SM; Shin-Etsu Chemical Co., Ltd.), ethyl cellulose (e.g., Emulfree CBG; Ikeda Corporation), hydroxyethyl cellulose (e.g., Cellosize series QP4400H and QP52000H; Dow Chemical Japan Limited, SE-600, SE-850, and SE-900; Daicel Chemical Industries, Ltd.), hydroxypropyl cellulose (e.g., Nisso series HPC-H and HPC-M; Nippon Soda Co., Ltd.), hydroxypropyl xanthan gum (e.g., Rhaball Gum EX; Sumitomo Dainippon Pharma Co., Ltd.), pullulan (e.g., Pullulan PF-20 and Pullulan PI-20; Hayashibara Co., Ltd.), and xanthan gum (e.g., Echo Gum; Sumitomo Dainippon Pharma Co., Ltd.). In addition, from the viewpoint that the influence on other components is small, nonionic polymer compounds are preferable, in particular, one or more selected from the group consisting of hydroxyethyl cellulose, methyl cellulose, xanthan gum, and hydroxypropyl xanthan gum are more preferable.

These thickeners can be used alone or in combination of two or more thereof. The content of the thickener in the hair cosmetic of the present invention is preferably 0.05 mass % or more, more preferably 0.1 mass % or more, and further preferably 0.5 mass % or more and preferably 20 mass % or less, more preferably 10 mass % or less, and further preferably 5 mass % or less from the viewpoint of adjusting the viscosity such that it can be uniformly applied to the hair of head and can be prevented from dripping.

[Surfactant]

The hair cosmetic of the present invention can contain a surfactant from the viewpoint of the feel and the dissolution performance. The surfactant may be any of a cationic surfactant, a nonionic surfactant, an amphoteric surfactant, and an anionic surfactant.

The cationic surfactant is preferably a mono-long-chain-alkyl quaternary ammonium salt, and examples thereof include cetrimonium chloride, steartrimonium chloride, behentrimonium chloride, stearalkonium chloride, and benzalkonium chloride.

Examples of the nonionic surfactant include a polyoxyalkylene alkyl ether, a polyoxyalkylene alkenyl ether, a higher fatty acid sucrose ester, a polyglycerol fatty acid ester, a higher fatty acid mono- or di-ethanol amide, a polyoxyethylene hydrogenated castor oil, a polyoxyethylene sorbitan fatty acid ester, a polyoxyethylene sorbit fatty acid ester, an alkyl saccharide, an alkylamine oxide, and an alkylamidoamine oxide.

Examples of the amphoteric surfactant include imidazoline, carbobetaine, amidobetaine, sulfobetaine, hydroxysulfobetaine, and amidosulfobetaine.

Examples of the anionic surfactant include an alkyl benzene sulfonate, an alkyl or alkenyl ether sulfate, an alkyl or alkenyl sulfate, an olefin sulfonate, an alkane sulfonate, a saturated or unsaturated fatty acid salt, an alkyl or alkenyl ether carboxylate, an α-sulfo fatty acid salt, an N-acyl amino acid, a phosphoric acid mono- or di-ester, and a sulfosuccinic acid ester. Examples of the alkyl ether sulfate include a polyoxyethylene alkyl ether sulfate. Examples of the counter ion of the anionic group of such an anionic surfactant include an alkali metal ion, such as a sodium ion and a potassium ion; an alkaline earth metal ion, such as a calcium ion and a magnesium ion; an ammonium ion; and an alkanol amine having one to three C2-C3 alkanol group (e.g., monoethanolamine, diethanolamine, triethanolamine, and triisopropanolamine).

These surfactants can be used alone or in combination of two or more thereof. The content of the surfactant in the hair cosmetic of the present invention is preferably 0.1 mass % or more, more preferably 0.2 mass % or more, and further preferably 0.5 mass % or more, and it is preferably 30 mass % or less, more preferably 20 mass % or less, and further preferably 15 mass % or less from the viewpoint of improving the feel and the solubility.

[Other Optional Components]

The hair cosmetic of the present invention can further contain other components that are usually used as cosmetic raw materials as long as the stable liquid state and the function as a hair cosmetic are not impaired. Examples of the optional component include a penetration enhancer, a pearling agent, a preservative, a metal sequestering agent, a stabilizer, an antioxidant, an ultraviolet absorber, a moisturizing agent, and an odor control agent, specifically, a higher alcohol, a higher fatty acid, a fatty acid ester, a hydrocarbon oil, a silicone, a protein hydrolysate, a protein derivative, an amino acid, a plant extract, a vitamin, and a perfume.

[pH]

The pH of the hair cosmetic of the present invention is preferably 3.0 or higher, more preferably 3.5 or higher, and further preferably 4.0 or higher from the viewpoint of reducing the irritation, and it is preferably 6.0 or lower and more preferably 5.0 or lower from the viewpoint of irritation suppression and prolonged pH stability.

Examples of the pH adjuster for adjusting the pH of the hair cosmetic to the above-mentioned level include acids such as inorganic acids (e.g., hydrochloric acid and phosphoric acid), organic acids (e.g., citric acid, glycolic acid, and lactic acid), ammonium chloride; hydrochlorides (e.g., monoethanolamine hydrochloride), phosphates (e.g., potassium dihydrogen phosphate and disodium hydrogen phosphate); alkali metal hydroxides (e.g., sodium hydroxide and potassium hydroxide); carbonates (e.g., sodium carbonate, potassium carbonate, sodium hydrogen carbonate, potassium hydrogen carbonate, guanidine carbonate).

[Viscosity]

The viscosity of the hair cosmetic of the present invention is preferably 10 mPa·s or higher, more preferably 50 mPa·s or higher, and further preferably 100 mPa·s or higher from the viewpoint of applicability to hair and prevention of dripping from hands or hair, and it is preferably 4,000 mPa·s or lower, more preferably 3,000 mPa·s or lower, and further preferably 2,000 mPa·s or lower from the viewpoint of ease of spreading on hair. Here in the present invention, the viscosity is the value measured with a B-type viscometer at 30° C. after rotation at 60 rpm for 1 minute. The rotor and the rotation rate in the measurement are selected in accordance with the manual of the measuring machine for appropriate conditions according to the viscosity of the hair cosmetic.

[Form]

The form of the hair cosmetic of the present invention is, for example, a liquid, a gel, a paste, a cream, or a wax form and can be appropriately selected, and the hair cosmetic is preferably a liquid in which water or a lower alcohol, in particular, water is used as a solvent.

[Usage]

The hair cosmetic of the present invention may be applied to dry hair or may be applied to wet hair, and it is preferable to apply to dry hair from the viewpoint of mitigating the hair swelling, suppressing the hair spread, and further improving the manageability and feel of the hair.

The amount of the hair cosmetic applied to hair is, as the bath ratio relative to the mass of the hair (mass of the hair cosmetic/mass of the hair), preferably 0.05 or more, more preferably 0.1 or more, further preferably 0.2 or more, further preferably 0.3 or more and preferably 2.0 or less, more preferably 1.5 or less, and further preferably 1.0 or less from the viewpoint of suppressing the hair spread and further improving the manageability and feel of the hair. The hair to which the hair cosmetic is applied may be all or part of the hair of head. For example, applying the hair cosmetic to severely damaged tips of hair enables to suppress the hair spread and further improve the hair manageability.

In order to spread the hair cosmetic to the entire hair of head after the application of the hair cosmetic to the hair, a method of using a hand, such as rubbing the hair cosmetic into hair or passing a hand comb through hair, a method of using a tool, such as a brush, a comb or a hairbrush, or a combination thereof may be used.

The hair after application of the hair cosmetic is preferably left to stand for a certain period of time from the viewpoint of further improving the manageability and feel of the hair. The temperature for the leaving is preferably 15° C. or higher and preferably 100° C. or lower, more preferably 60° C. or lower, and further preferably 30° C. or lower. A temperature of 15° C. or higher and lower than 30° C., i.e., room temperature is preferred because the treatment with the hair cosmetic is simple without requiring specific equipment. In contrast, from the viewpoint of shortening the time for the leaving, the hair can also be left to stand while heating with a heater or the like, and the temperature in such a case is preferably 30° C. or higher, more preferably 40° C. or higher and preferably 100° C. or lower, more preferably 60° C. or lower.

The time for leaving the hair to which the hair cosmetic has been applied is preferably 15 seconds or more, more preferably 30 seconds or more, further preferably 1 minute or more, further preferably 3 minutes or more, and further preferably 5 minutes or more, and is preferably 60 minutes or less, more preferably 45 minutes or less, and further preferably 30 minutes or less from the viewpoint of further improving the manageability and feel of the hair. As described above, when the hair is left to stand while heating with a heater or the like, the time for the leaving can be further shortened, in which case it is preferably 15 seconds or more, more preferably 30 seconds or more, further preferably 1 minute or more, further preferably 3 minutes or more, and further preferably 5 minutes or more, and is preferably 30 minutes or less, more preferably 15 minutes or less, and further preferably 10 minutes or less. After the leaving of the hair to which the hair cosmetic has been applied for the above-mentioned period of time, the hair cosmetic is preferably not washed off from the hair from the viewpoint of further improving the manageability and feel of the hair.

The hair cosmetic of the present invention is preferably used as a hair conditioning agent, such as a hair treatment agent, or a hair styling agent and is, in particular, preferably used together with a hair bleaching agent or oxidative hair dyeing agent including a first agent containing an alkaline agent and a second agent containing an oxidizing agent from the viewpoint of reducing the hair swelling occurring by the chemical treatment for bleaching or dyeing the hair, suppressing the hair spread, and further improving the hair manageability. In such a case, the hair cosmetic of the present invention is preferably provided as a hair bleaching or dyeing kit including the hair cosmetic of the present invention and the hair bleaching agent or oxidative hair dyeing agent. It is inferred that when the hair cosmetic of the present invention is used together with a hair bleaching agent or an oxidative hair dyeing agent, the components contained in the hair cosmetic of the present invention penetrate deeper into the hair by the action of the alkaline agent contained in the hair bleaching agent or oxidative hair dyeing agent to swell the hair and contribute to further improvement in the manageability and feel of the hair. Examples of the dosage form of the hair cosmetic of the present invention include a pump spray, an aerosol spray, a pump foam, an aerosol foam, a gel, and a lotion.

In a case that the hair cosmetic of the present invention is used together with a hair bleaching agent or an oxidative hair dyeing agent, both may be mixed at the time of use and the resulting mixture may be applied to the hair, and it is preferable that both are separately applied to the hair. In such a case, the hair cosmetic of the present invention may be applied to the hair before the use of the hair bleaching agent or the oxidative hair dyeing agent or may be applied to the hair after the use of the hair bleaching agent or the oxidative hair dyeing agent, and also both may be performed. In particular, from the viewpoint of reducing the hair swelling, suppressing the spread of the hair, and further improving the manageability and feel of the hair, it is preferable that the hair cosmetic be applied to the hair before the use of the hair bleaching agent or the oxidative hair dyeing agent, that is, the hair cosmetic is used as a pretreatment agent for the hair bleaching agent or the oxidative hair dyeing agent.

[Method for Bleaching or Dyeing Hair]

The method for bleaching or dyeing hair of the present invention includes the following steps (i) and (ii):
(i) a step of applying the hair cosmetic of the present invention to hair; and
(ii) a step of applying a solution mixture of a first agent containing an alkaline agent and a second agent containing an oxidizing agent of a hair bleaching agent or an oxidative hair dyeing agent to the hair after the step (i).

<Step (i)>

The step (i) is performed by the method as described in the paragraph "Usage".

<Step (ii)>

The step (ii) is a hair bleaching or dyeing treatment by applying a mixture of the first agent and the second agent as a hair bleaching agent or an oxidative hair dyeing agent (hereinafter, simply referred to as "hair bleaching or dyeing agent mixture") to the hair and may be performed as in hair bleaching or dyeing treatment with an ordinary hair bleaching agent or oxidative hair dyeing agent.

The temperature when the hair bleaching or dyeing agent mixture is applied to hair in the step (ii) is preferably from 15° C. to 45° C., and the amount of the hair bleaching or dyeing agent mixture applied to hair is, as the bath ratio relative to the mass of the hair (mass of the hair bleaching or dyeing agent mixture/mass of the hair), preferably 0.1 or more, more preferably 0.3 or more, and further preferably 0.5 or more, and is preferably 5.0 or less, more preferably 3.0 or less, and further preferably 2.0 or less.

The mass ratio of the amount of the hair cosmetic applied to hair in the step (i) to the amount of the hair bleaching or dyeing agent mixture applied to the hair in the step (ii), (hair cosmetic)/(hair bleaching or dyeing agent mixture), is preferably 0.02 or more, more preferably 0.1 or more, and further preferably 0.2 or more, and is preferably 15 or less, more preferably 10 or less, and further preferably 5.0 or less from the viewpoint of further improving the manageability and feel of the hair.

The hair bleaching or dyeing agent mixture applied to hair is preferably left to stand on the hair for a certain period of time. The time for the leaving is preferably 1 minute or more and more preferably 5 minutes or more, and is preferably 60 minutes or less, more preferably 45 minutes or less, and further preferably 30 minutes or less. After the leaving, the hair bleaching or dyeing agent mixture on the hair is washed off with water, and the hair can be optionally shampooed and dried.

As the hair cosmetic that is used before a hair bleaching agent or an oxidative hair dyeing agent is applied to hair, not only the hair cosmetic of the present invention but also that containing the above-mentioned component (C) only or that containing the above-mentioned components (C) and (B) has the effects of reducing the hair swelling, suppressing the hair spread, and improving the manageability and feel of the hair. That is, the hair cosmetic containing the component (C) or the hair cosmetic containing the components (C) and (B) can also be used as the hair cosmetic in the hair bleaching or dyeing kit, the pretreatment agent for the hair bleaching agent or the oxidative hair dyeing agent, or the hair cosmetic used in the method for bleaching or dyeing hair.

Regarding the embodiments described above, preferred aspects of the present invention will be further disclosed below:

<1> A hair cosmetic comprising the following components (A) and (B) at a mass ratio of component (B) to component (A), (B)/(A), of from 0.7 to 5.0:
(A) an aromatic sulfonic acid having a molecular weight of 300 or less or a salt thereof: 0.05 to 5 mass %,
(B) a cationic polymer having a cationic charge density of 4.5 meq/g or more: 0.1 to 20 mass %.

<2> A hair cosmetic comprising the following components (A) and (B) at a mass ratio of component (B) to component (A), (B)/(A), of from 1.0 to 3.0:
(A) an aromatic sulfonic acid having a molecular weight of 300 or less or a salt thereof,
(B) a cationic polymer having a cationic charge density of from 4.5 to 25 meq/g.

<3> A hair cosmetic comprising the following components (A) and (B) at a mass ratio of component (B) to component (A), (B)/(A), of from 0.7 to 5.0:
(A) at least one selected from the group consisting of p-toluenesulfonic acid, xylenesulfonic acid, 2-naphthalenesulfonic acid, 1-naphthalenesulfonic acid, and hydroxymethoxybenzophenonesulfonic acid, and a salt thereof,
(B) a cationic polymer having a cationic charge density of 4.5 meq/g or more and a molar fraction of a dimethyl diallyl quaternary ammonium salt monomer of 70% or more.

<4> The hair cosmetic according to <2> or <3>, wherein the content of component (A) is preferably from 0.05 to 5 mass %, more preferably from 0.10 to 2.0 mass %, further preferably from 0.20 to 1.5 mass %, further preferably from 0.30 to 1.2 mass %, further preferably from 0.50 to 1.2 mass %, and further preferably from 0.80 to 1.2 mass %.

<5> The hair cosmetic according to any one of <2> to <4>, wherein the content of component (B) is preferably from 0.1 to 20 mass % more preferably from 0.2 to 10 mass %, further preferably from 0.3 to 5 mass %, further preferably from 0.5 to 3 mass %, further preferably from 1.0 to 2.5 mass %, and further preferably from 1.5 to 2.3 mass %.

<6> The hair cosmetic according to any one of <1> to <5>, wherein component (B) preferably has a cationic charge density of from 4.5 to 20 meq/g, more preferably from 4.5 to 15 meq/g, further preferably from 4.5 to 7.0 meq/g, further preferably from 4.8 to 6.5 meq/g, and further more preferably from 5.6 to 6.2 meq/g.

<7> The hair cosmetic according to any one of <1> to <6>, preferably further comprising the following component (C), (C) a compound represented by the following formula (4) or a salt thereof:

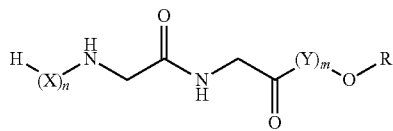

(4)

wherein X represents a divalent C1-C4 hydrocarbon group optionally substituted with a hydroxy group or an amino acid residue, and Y represents an amino acid residue or a divalent group represented by the following chemical formula (5):

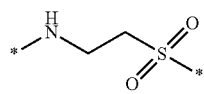

(5)

(wherein -* represents a bond that binds to an adjacent carbonyl group or oxygen atom); R represents a hydrogen atom or a monovalent C1-C4 hydrocarbon group optionally substituted with a hydroxy group; and m and n each represent 0 or 1 provided that when m and n are both 1, X is not an amino acid residue.

<8> The hair cosmetic according to any one of <1> to <7>, preferably being a hair treatment agent.

<9> The hair cosmetic according to any one of <1> to <8>, preferably being a hair bleaching or oxidative hair dyeing pretreatment agent to be used before a hair bleaching agent or oxidative hair dyeing agent comprising a first agent comprising an alkaline agent and a second agent comprising an oxidizing agent is applied to hair.

<10> A hair bleaching or dyeing kit comprising the hair cosmetic according to any one of <1> to <9> and a hair bleaching agent or oxidative hair dyeing agent comprising a first agent comprising an alkaline agent and a second agent comprising an oxidizing agent.

<11> The hair bleaching or dyeing kit according to <10>, wherein the hair cosmetic is preferably used before the hair bleaching agent or oxidative hair dyeing agent is applied to hair.

<12> Use of the hair cosmetic according to any one of <1> to <8> as a pretreatment agent for a hair bleaching agent or oxidative hair dyeing agent comprising a first agent comprising an alkaline agent and a second agent comprising an oxidizing agent.

<13> A method for bleaching or dyeing hair, comprising the following steps (i) and (ii):

(i) a step of applying the hair cosmetic according to any one of <1> to <8> to hair; and (ii) a step of applying a solution mixture of a first agent comprising an alkaline agent and a second agent comprising an oxidizing agent of a hair bleaching agent or an oxidative hair dyeing agent to the hair after the step (i).

<14> A hair cosmetic comprising the following components (A) and (B) at a mass ratio of component (B) to component (A), (B)/(A), of from 0.7 to 5.0:

(A) an aromatic sulfonic acid having a molecular weight of 300 or less or a salt thereof: 0.8 to 5 mass %, (B) a cationic polymer having a cationic charge density of 4.5 meq/g or more: 0.1 to 20 mass %.

<15> A hair cosmetic comprising the following components (A) and (B) at a mass ratio of component (B) to component (A), (B)/(A), of from 1.0 to 5.0:

(A) an aromatic sulfonic acid having a molecular weight of 300 or less or a salt thereof: 0.8 to 5 mass %, (B) a cationic polymer having a cationic charge density of 4.5 meq/g or more: 0.1 to 20 mass %.

<16> A hair cosmetic comprising the following components (A) and (B) at a mass ratio of component (B) to component (A), (B)/(A), of from 0.7 to 4.5:

(A) an aromatic sulfonic acid having a molecular weight of 300 or less or a salt thereof: 0.8 to 3.0 mass %, (B) a cationic polymer having a cationic charge density of 4.5 meq/g or more: 0.5 to 8 mass %.

<17> A hair cosmetic comprising the following components (A) and (B) at a mass ratio of component (B) to component (A), (B)/(A), of from 1.0 to 3.0:

(A) an aromatic sulfonic acid having a molecular weight of 300 or less or a salt thereof: 0.8 to 2.0 mass %, (B) a cationic polymer having a cationic charge density of 4.5 meq/g or more: 0.5 to 5 mass %.

<18> A hair cosmetic comprising the following components (A) and (B) at a mass ratio of component (B) to component (A), (B)/(A), of from 1.5 to 2.5:

(A) an aromatic sulfonic acid having a molecular weight of 300 or less or a salt thereof: 0.8 to 2.0 mass %, (B) a cationic polymer having a cationic charge density of 4.5 meq/g or more: 0.5 to 5 mass %.

<19> The hair cosmetic according to any one of <14> to <18>, wherein component (A) includes a benzenesulfonic acid represented by formula (1):

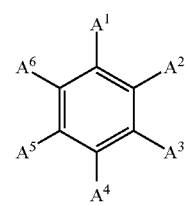

(1)

wherein at least one of $A^1$ to $A^6$ represents a sulfo group or a salt thereof, and the remainder are each a hydrogen atom or a C1-C3 alkyl group.

<20> The hair cosmetic according to any one of <14> to <19>, wherein component (A) includes at least one selected from the group consisting of p-toluenesulfonic acid, xylenesulfonic acid, 2-naphthalenesulfonic acid, 1-naphthalenesulfonic acid, and hydroxymethoxybenzophenonesulfonic acid, and a salt thereof.

<21> The hair cosmetic according to any one of <14> to <20>, wherein component (A) includes p-toluenesulfonic acid.

<22> The hair cosmetic according to any one of <14> to <21>, wherein component (B) includes a cationic polymer having a cationic charge density of from 4.5 to 7.0 meq/g.

<23> The hair cosmetic according to any one of <14> to <22>, wherein component (B) includes a cationic polymer having a cationic charge density of from 4.8 to 6.5 meq/g.

<24> The hair cosmetic according to any one of <14> to <23>, wherein component (B) includes one or more selected from the group consisting of a dimethyldiallylammonium chloride polymer and a dimethyldiallylammonium chloride-acrylic acid copolymer.

<25> The hair cosmetic according to any one of <14> to <24>, having a pH of from 3.0 to 6.0.

<26> The hair cosmetic according to any one of <14> to <25>, having a pH of from 3.5 to 5.0.

<27> The hair cosmetic according to any one of <14> to <26>, having a pH of from 4.0 to 5.0.

<28> The hair cosmetic according to any one of <14> to <27>, being a hair treatment agent.

<29> A hair bleaching kit or a hair dyeing kit composed of the hair cosmetic according to any one of <14> to <28> and a hair bleaching agent or oxidative hair dyeing agent comprising a first agent comprising an alkaline agent and a second agent comprising an oxidizing agent.

<30> A method for treating hair by applying the hair cosmetic according to any one of <14> to <28> to hair before a hair bleaching agent or oxidative hair dyeing agent comprising a first agent comprising an alkaline agent and a second agent comprising an oxidizing agent is applied to the hair.

<31> Use of the hair cosmetic according to any one of <14> to <28> as a pretreatment agent for a hair bleaching agent or oxidative hair dyeing agent comprising a first agent containing an alkaline agent and a second agent comprising an oxidizing agent.

<32> A method for bleaching or dyeing hair, comprising the following steps (i) and (ii):
(i) a step of applying the hair cosmetic according to any one of <14> to <28> to hair; and
(ii) a step of applying a solution mixture of a first agent comprising an alkaline agent and a second agent comprising an oxidizing agent of a hair bleaching agent or an oxidative hair dyeing agent to the hair after the step (i).

<33> A method for bleaching or dyeing hair, comprising a step of applying a solution mixture of the hair cosmetic according to any one of <14> to <28>, a first agent for a hair bleaching agent or oxidative hair dyeing agent comprising an alkaline agent, and a second agent for a hair bleaching agent or oxidative hair dyeing agent comprising an oxidizing agent to hair.

<34> A method for bleaching or dyeing hair, comprising the following steps (i) and (ii):
(i) a step of applying a solution mixture of a first agent comprising an alkaline agent and a second agent comprising an oxidizing agent of a hair bleaching agent or an oxidative hair dyeing agent to hair; and
(ii) a step of applying the hair cosmetic according to any one of <14> to <28> to the hair after the step (i).

EXAMPLES

Examples 1 to 14 and Comparative Examples 1 to 11

Treatment agents were prepared according to the prescription shown in Tables 1 to 3, and the performance thereof was evaluated by the following methods. The results of the evaluation are collectively shown in the tables.

<Method for Treating Hair>
(i) A tress having a length of about 25 to 30 cm and a weight of 0.2 g was prepared by arranging Japanese female hair (hair being slightly frizzy and slightly thicker than average hair and being from a single person) in a width of about 5 mm and fixing the upper end. This tress was washed with a washing shampoo having the composition shown below and then was suspended by fixing the upper end to dry, and the shape of the dried hair was then photographed. Tress used in Examples and Comparative Examples all had a width within a range of from 2.8 to 5.8 cm and a length within a range of from 25 to 28.5 cm. Incidentally, the width refers to the dimension of the widest part of the suspended tress.

(ii) Subsequently, each of the treatment agents shown in Tables 1 to 3 was applied to the hair above at a bath ratio of 1:1, and the hair was placed at 30° C. for 5 minutes and then treated with running water for 30 seconds, washed with shampoo, and treated with a conditioner. Then, in the state of being fixed at the upper end of the hair, hand blowing was performed while blowing hot air with a dryer, and the condition of the dried hair was photographed.

(iii) Finally, in order to verify the persistence of the effects, the hair above was washed with shampoo 7 times, and then, in the state of being fixed at the upper end of the hair, hand blowing was performed while blowing hot air with a dryer, and the condition of the dried hair was photographed.

The hair after the treatments (i) to (iii) were defined as the conditions of the hair "before treatment", "immediately after treatment", and "after washing with shampoo 7 times", respectively. In addition, the hair used was all from a single person. The photographing was performed by taking a picture of the entire hair in the state of being fixed at the upper end of the hair and suspended with a camera from a distance of about 45 cm. On this occasion, the recording was performed such that the positions of the hair and the camera were the same in the before treatment, the immediately after treatment, and the after washing with shampoo 7 times.

<Washing Shampoo Composition> (Composition on an as-is Basis)

Sodium lauryl sulfate (Emal 227, Kao Corporation): 57.00 mass %

Lauramide DEA (Aminone L-02, Kao Corporation): 1.50 mass %

Sodium benzoate (Na Benzoate Aqueous Solution 35%, Aioi ChemiScience Co., Ltd.): 1.40 mass %

Disodium EDTA (Clewat N, Nagase ChemteX Corporation): 0.30 mass %

Phosphoric acid (Food Additive 75% Phosphoric acid, Nippon Chemical Industrial Co., Ltd.): 0.02 mass %

Purified water: 39.78 mass %

Method for Evaluating Manageability

The manageability was evaluated by comparing the degrees of spread of the hair tress after each treatment based on the photographed images. Specifically, the width of the tress after each treatment was measured, and the rates of change in the width immediately after treatment and after washing with shampoo 7 times were calculated assuming that the width of the hair before the treatment was 1. A smaller rate of change indicates that the spread of the tress is more suppressed, the swelling is more suppressed, which means a high hair-managing effect. In addition, the retention of a smaller rate of change until after shampooing 7 times indicates a higher duration of the effect.

<Evaluation of Physical Properties of Coating Film>

The physical properties of the coating film formed from component (A) and a cationic polymer such as component (B) were evaluated as follows. Incidentally, this evaluation was performed by mixing p-toluenesulfonic acid and a cationic polymer (on an as-is basis) as raw materials shown in the tables.

P-toluenesulfonic acid and each product of various cationic polymers were weighed in a petri dish having a diameter of 3 cm so as to have a mass ratio of the active ingredients shown in the tables, sufficiently mixed, and then dried in an oven of 50° C. for 48 hours to form each coating film. One panelist touched each coating film with a finger to evaluate three points: adhesiveness, softness, and elasticity (toughness) according to the following criteria. Incidentally, Caticello L150 used in Comparative Examples 10 and 11 was a powder and was therefore made into a 3 mass % aqueous solution and then mixed with component (A).

Adhesiveness

From the viewpoint of the difficulty in separating from a finger after the coating film was pushed with the finger, the adhesiveness was evaluated according to the following four criteria:

1: very difficult to separate from the finger and very adhesive,

2: difficult to separate from the finger and adhesive,

3: slightly difficult to separate from the finger and slightly adhesive, and

4: easy to separate from the finger and not adhesive.

Softness

From the viewpoint of the degree of deformation of the coating film when pushed with a finger, the softness was evaluated according to the following four criteria:

1: very deformable and very soft,

2: deformable and soft,

3: slightly deformable and slightly soft, and

4: difficult to deform and hard.

Elasticity (Toughness)

From the viewpoint of the difficulty in tearing and the elasticity of the coated film when scooped with a spatula, the elasticity was evaluated according to the following four criteria:

1: very difficult to tear, very elastic and tough,

2: difficult to tear, elastic and tough,

3: slightly difficult to tear, slightly elastic and slightly tough, and

4: easy to tear, not elastic and fragile.

TABLE 1

| (mass %: on an as-is basis) | | | Example 1 | Example 2 | Comparative Example 1 | Comparative Example 2 |
|---|---|---|---|---|---|---|
| Composition | (A) | p-Toluenesulfonic acid [*1] | 1.60 | 1.60 | 1.60 | — |
| | (B) | Polyquaternium-6 [*2] | 4.83 | 4.83 | — | 4.83 |
| | (C) | Glycylglycine [*3] | — | 1.20 | — | — |
| | Others | 95% Ethanol | 10.00 | 10.00 | 10.00 | 10.00 |
| | | Methylparaben | 0.10 | 0.10 | 0.10 | 0.10 |
| | | 48% Sodium hydroxide | 0.11 | 0.11 | 0.11 | 0.11 |
| | | Purified water | 83.37 | 82.17 | 88.20 | 84.97 |
| | | Total | 100.00 | 100.00 | 100.00 | 100.00 |
| Active ingredient | Component (A) content (mass %) | | 1.00 | 1.00 | 1.00 | 0.00 |
| | Component (B) content (mass %) | | 2.00 | 2.00 | 0.00 | 2.00 |
| | (B)/(A) mass ratio | | 2.00 | 2.00 | 0.00 | — |
| Evaluation | Formation of coating film | | Formed | Formed | Not formed | Formed |
| | Coating film physical properties | Adhesiveness | 1 | 1 | — | 4 |
| | | Softness | 2 | 2 | — | 4 |
| | | Elasticity (toughness) | 1 | 1 | — | 1 |
| | Hair-managing effect | Immediately after treatment | 0.56 | 0.33 | 0.83 | 0.89 |
| | | After shampooing 7 times | 0.50 | 0.38 | 1.00 | 0.89 |

TABLE 2

| (mass %: on an as-is basis) | | | Example 3 | Example 4 | Example 5 | Example 6 | Example 7 | Example 8 | Example 9 |
|---|---|---|---|---|---|---|---|---|---|
| Composition | (A) | p-Toluenesulfonic acid [*1] | 1.60 | 1.60 | 1.60 | 1.60 | 1.60 | 1.60 | 3.20 |
| | (B) | Polyquaternium-6 [*2] | 1.92 | 2.41 | 3.62 | 6.03 | 9.65 | 12.06 | 4.83 |
| | Others | 95% Ethanol | 10.00 | 10.00 | 10.00 | 10.00 | 10.00 | 10.00 | 10.00 |
| | | Methylparaben | 0.10 | 0.10 | 0.10 | 0.10 | 0.10 | 0.10 | 0.10 |
| | | 48% Sodium hydroxide | 0.11 | 0.11 | 0.11 | 0.11 | 0.11 | 0.11 | 0.11 |
| | | Purified water | 86.27 | 85.79 | 84.58 | 82.17 | 78.54 | 76.13 | 81.76 |
| | | Total | 100.00 | 100.00 | 100.00 | 100.00 | 100.00 | 100.00 | 100.00 |
| Active ingredient | Component (A) content (mass %) | | 1.00 | 1.00 | 1.00 | 1.00 | 1.00 | 1.00 | 2.00 |
| | Component (B) content (mass %) | | 0.80 | 1.00 | 1.50 | 2.50 | 4.00 | 5.00 | 2.00 |
| | (B)/(A) mass ratio | | 0.80 | 1.00 | 1.50 | 2.50 | 4.00 | 5.00 | 1.00 |
| Evaluation | Formation of coating film | | Formed | Formed | Formed | Formed | Formed | Formed | Formed |
| | Coating film physical properties | Adhesiveness | — | 2 | 1 | 1 | — | — | — |
| | | Softness | — | 1 | 1 | 2 | — | — | — |
| | | Elasticity (toughness) | — | 2 | 2 | 1 | — | — | — |

TABLE 2-continued

|  |  | | | | | | | |
|---|---|---|---|---|---|---|---|---|
| Hair-managing effect | Immediately after treatment | 0.67 | 0.70 | 0.58 | 0.77 | 0.75 | 0.79 | 0.73 |
|  | After shampooing 7 times | 0.72 | 0.79 | 0.75 | 0.69 | 0.75 | 0.79 | 0.73 |

|  |  |  | Example | | | Comparative Example | | | |
|---|---|---|---|---|---|---|---|---|---|
| (mass %: on an as-is basis) | | | 10 | 11 | 12 | 3 | 4 | 5 | 6 |
| Composition | (A) | p-Toluenesulfonic acid (*1) | 1.28 | 1.05 | 0.64 | 1.60 | 1.60 | 0.32 | 0.21 |
|  | (B) | Polyquaternium-6 (*2) | 4.83 | 4.83 | 4.83 | 0.48 | 1.20 | 4.83 | 4.83 |
|  | Others | 95% Ethanol | 10.00 | 10.00 | 10.00 | 10.00 | 10.00 | 10.00 | 10.00 |
|  |  | Methylparaben | 0.10 | 0.10 | 0.10 | 0.10 | 0.10 | 0.10 | 0.10 |
|  |  | 48% Sodium hydroxide | 0.11 | 0.11 | 0.11 | 0.11 | 0.11 | 0.11 | 0.11 |
|  |  | Purified water | 83.68 | 83.92 | 84.33 | 87.72 | 87.00 | 84.65 | 84.75 |
|  | Total |  | 100.00 | 100.00 | 100.00 | 100.00 | 100.00 | 100.00 | 100.00 |
| Active ingredient | Component (A) content (mass %) | | 0.80 | 0.66 | 0.40 | 1.00 | 1.00 | 0.20 | 0.13 |
|  | Component (B) content (mass %) | | 2.00 | 2.00 | 2.00 | 0.20 | 0.50 | 2.00 | 2.00 |
|  | (B)/(A) mass ratio | | 2.50 | 3.05 | 5.00 | 0.20 | 0.50 | 10.01 | 15.03 |
| Evaluation | Formation of coating film | | Formed | Formed | Formed | Formed | Formed | Formed | Formed |
|  | Coating film physical properties | Adhesiveness | — | 3 | 3 | 1 | 2 | — | — |
|  |  | Softness | — | 3 | 3 | 1 | 1 | — | — |
|  |  | Elasticity (toughness) | — | 1 | 1 | 4 | 3 | — | — |
|  | Hair-managing effect | Immediately after treatment | 0.79 | 0.73 | 0.74 | 0.87 | 0.85 | 1.04 | 0.96 |
|  |  | After shampooing 7 times | 0.79 | 0.96 | 1.03 | 0.87 | 0.85 | 1.13 | 0.93 |

TABLE 3

|  |  |  | Example | | Comparative Example | | | | |
|---|---|---|---|---|---|---|---|---|---|
| (mass %: on an as-is basis) | | | 13 | 14 | 7 | 8 | 9 | 10 | 11 |
| Composition | (A) | p-Toluenesulfonic acid (*1) | 1.60 | 1.60 | 1.60 | 1.60 | 1.60 | 1.60 | 1.60 |
|  | (B) | Polyquaternium-22 (*4) | 5.33 | — | — | — | — | — | — |
|  |  | Polyquaternium-22 (*5) | — | 4.88 | — | — | — | — | — |
|  | (B') | Polyquaternium-7 (*6) | — | — | 22.21 | — | — | — | — |
|  |  | Polyquaternium-47 (*7) | — | — | — | 4.80 | 2.40 | — | — |
|  |  | Polyquaternium-1 (*8) | — | — | — | — | — | 2.00 | 0.50 |
|  | Others | 95% Ethanol | 10.00 | 10.00 | 10.00 | 10.00 | 10.00 | 10.00 | 10.00 |
|  |  | Methylparaben | 0.10 | 0.10 | 0.10 | 0.10 | 0.10 | 0.10 | 0.10 |
|  |  | 48% Sodium hydroxide | 0.11 | 0.11 | 0.11 | 0.11 | 0.11 | 0.11 | 0.11 |
|  |  | Purified water | 82.87 | 83.32 | 65.99 | 83.40 | 85.80 | 86.20 | 87.70 |
|  | Total | | 100.00 | 100.00 | 100.00 | 100.00 | 100.00 | 100.00 | 100.00 |
| Active ingredient | Component (A) content (mass %) | | 1.00 | 1.00 | 1.00 | 1.00 | 1.00 | 1.00 | 1.00 |
|  | Component (B) content (mass %) | | 2.00 | 2.00 | 2.00 | 1.00 | 0.50 | 2.00 | 0.50 |
|  | (B)/(A) mass ratio | | 2.00 | 2.00 | 2.00 | 1.00 | 0.50 | 2.00 | 0.50 |
| Evaluation | Formation of coating film | | Formed | Formed | Formed | Formed | Formed | Formed | Formed |
|  | Coating film physical properties | Adhesiveness | 2 | 3 | 4 | 3 | 2 | 3 | 3 |
|  |  | Softness | 2 | 2 | 4 | 3 | 1 | 1 | 1 |
|  |  | Elasticity (toughness) | 1 | 2 | 4 | 1 | 3 | 4 | 4 |
|  | Hair-managing effect | Immediately after treatment | 0.87 | 0.69 | 0.93 | 0.91 | 1.28 | 0.89 | 1.00 |
|  |  | After shampooing 7 times | 0.58 | 0.63 | 1.00 | 0.96 | 1.33 | 1.29 | 1.11 |

Examples 15 to 17

Hair treatment with the treatment agent of Example 1 was performed in combination with hair dyeing treatment with the two-agent type oxidative hair dyeing agent shown in Table 4, and the hair manageability was evaluated in the same manner as in Example 1. The results of the evaluation are shown in Table 5.

<Method for Treating Hair>

A method for treating hair was performed in the same manner as in the method for treating hair performed in Example 1 except that the step (ii) was changed to a step (ii-a), (ii-b), or (ii-c) shown below. That is, when the hair treatment with a treatment agent was pretreatment for the hair dyeing treatment with a two-agent type oxidative hair dyeing agent, the step (ii) of the method for treating hair was changed to the step (ii-a); when the hair treatment was performed with a mixture of a treatment agent and a two-agent type oxidative hair dyeing agent, the step (ii) of the method for treating hair was changed to the step (ii-b); and when the hair treatment with a treatment agent was post-treatment for the hair dyeing treatment with a two-agent type oxidative hair dyeing agent, the step (ii) of the method for treating hair was changed to the step (ii-c).

(ii-a) [Pretreatment]

Next, the treatment agent according to Example 1 shown in Table 1 was applied to the hair above at a bath ratio (mass of the treatment agent/mass of the hair) of 0.22, the first agent and the second agent of the two-agent type oxidative hair dyeing agent shown in Table 4 was then mixed at a mass ratio of 1:1, and the mixture was applied to the hair at an amount such that the ratio (application amount of the treatment agent)/(application amount of the hair dyeing agent mixture) was 0.22, followed by leaving to stand at 30° C. for 20 minutes. Subsequently, treatment with running water for 30 seconds, washing with shampoo, and treatment with a conditioner were performed. Then, in the state of being fixed at the upper end of the hair, hand blowing was performed while blowing hot air with a dryer, and the condition of the dried hair was photographed.

(ii-b) [Simultaneous Treatment]

Next, the two-agent type oxidative hair dyeing agent shown in Table 4 and the treatment agent according to Example 1 shown in Table 1 were mixed at a mass ratio of first agent:second agent:treatment agent of 1:1:0.44, and the mixture was applied to the hair above at a bath ratio (mass of the mixture of two-agent type oxidative hair dyeing agent and treatment agent/mass of the hair) of 1.22, followed by leaving to stand at 30° C. for 20 minutes. Subsequently, treatment with running water for 30 seconds, washing with shampoo, and treatment with a conditioner were performed. Then, in the state of being fixed at the upper end of the hair, hand blowing was performed while blowing hot air with a dryer, and the condition of the dried hair was photographed.

(ii-c) [Posttreatment]

Then, the first agent and the second agent of the two-agent type oxidative hair dyeing agent shown in Table 4 were mixed at a mass ratio of 1:1, the mixture was applied to the hair above at a bath ratio (mass of the hair dyeing agent/mass of hair) of 1, and the treatment agent according to Example 1 shown in Table 1 was then applied to the hair at an amount such that the ratio (application amount of the treatment agent)/(application amount of the hair dyeing agent mixture) was 0.22, followed by leaving to stand at 30° C. for 20 minutes. Subsequently, treatment with running water for 30 seconds, washing with shampoo, and treatment with a conditioner were performed. Then, in the state of being fixed at the upper end of the hair, hand blowing was performed while blowing hot air with a dryer, and the condition of the dried hair was photographed.

TABLE 4

|  | (mass %) |
| --- | --- |
| First agent (component) | |
| Meta-Aminophenol | 0.1 |
| Toluene-2,5-diamine | 1.0 |
| Resorcinol | 0.5 |
| EDTA-4Na | 0.1 |
| Ascorbic acid | 0.4 |
| Anhydrous sodium sulfite | 0.3 |
| Monoethanolamine | 3.0 |
| 28% Ammonia water | 2.0 |
| Water | 92.6 |
|  | 100.00 |
| Second agent (component) | |
| 35% Hydrogen peroxide | 16.29 |
| Steartrimonium chloride (*9) | 2.23 |
| Octyldodeceth-20 (*10) | 1.08 |
| Ceteth-40 (*11) | 0.75 |
| Ceteth-2 (*12) | 0.33 |
| Stearyl alcohol | 5.8 |
| Behenyl alcohol | 1.66 |
| Liquid paraffin (*13) | 10.17 |
| Concentrated glycerol | 3.0 |
| Lanolin fatty acid (*14) | 0.01 |
| 8-Quinolinol sulfate (*15) | 0.04 |
| Etidronic acid 60% aqueous solution (*16) | 0.08 |
| 48% Sodium hydroxide | 0.04 |
| Water | 58.52 |
|  | 100.00 |

(*9): Quartamin 86W (manufactured by Kao Corporation)
(*10): Emulgen 2020G (manufactured by Kao Corporation)
(*11): Nikkol BC-40TX (manufactured by Nippon Surfactant Industries Co., Ltd.)
(*12): Nikkol BC-2 (manufactured by Nippon Surfactant Industries Co., Ltd.)
(*13): Hicall K-350 (manufactured by Kaneda Co., Ltd.)
(*14): 18 MEA-SO- (RB) (manufactured by Croda Europe Ltd.)
(*15): 8-Quinolinol sulfate (manufactured by Nippon Rika Co., Ltd.)
(*16): Dequest 2010CS (manufactured by Italmatch Japan

TABLE 5

|  |  | Pre-treatment | Simultaneous treatment | Post-treatment |
| --- | --- | --- | --- | --- |
| Hair-managing effect | Immediately after treatment | 0.6 | 0.69 | 0.75 |
|  | After shampooing 7 times | 0.65 | 0.77 | 0.83 |

The invention claimed is:

1. A hair cosmetic, comprising:

(A) a benzenesulfonic acid represented by formula (1):

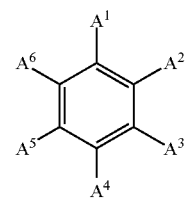

(1)

where at least one of $A^1$ to $A^6$ represents a sulfo group or a salt thereof, and the remainder are each a hydrogen atom or a C1-C3 alkyl group, provided said benzenesulfonic acid has a molecular weight of 300 or less or a salt thereof; and (B) a cationic polymer containing a dimethyl diallyl quaternary ammonium salt monomer and having a cationic charge density of 4.5 meq/g or more, wherein a mass ratio of the component (B) to the component (A), (B)/(A), is 0.7 or more and 5.0 or less.

2. The hair cosmetic according to claim 1, wherein the mass ratio of the component (B) to the component (A), (B)/(A), is 1.0 or more and 5.0 or less.

3. The hair cosmetic according to claim 1, wherein the component (B) has a cationic charge density of 4.5 meq/g or more and 25 meq/g or less.

4. The hair cosmetic according to claim 1, wherein a content of the component (B) is 20 mass % or less.

5. The hair cosmetic according to claim 1, further comprising:

(C) a compound represented by the formula (4) or a salt thereof:

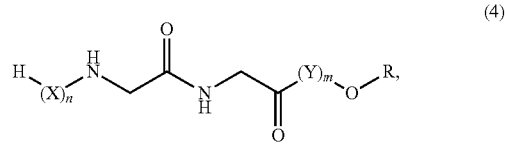

(4)

where X represents a divalent C1-C4 hydrocarbon group optionally substituted with a hydroxy group or an amino acid residue; Y represents an amino acid residue or a divalent group represented by the following chemical formula (5):

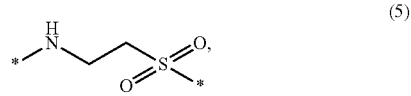

(5)

where -* represents a bond that binds to an adjacent carbonyl group or oxygen atom; R represents a hydrogen atom or a monovalent C1-C4 hydrocarbon group optionally substituted with a hydroxy group; and m and n each represent 0 or 1 provided that when m and n are both 1, X is not an amino acid residue.

6. The hair cosmetic according to claim 1, which is a hair treatment agent.

7. The hair cosmetic according to claim 1, which is a pretreatment agent suitable to be used before a hair bleaching agent or oxidative hair dyeing agent including a first agent comprising an alkaline agent and a second agent comprising an oxidizing agent is applied to hair.

8. A hair bleaching or dyeing kit, comprising:
the hair cosmetic according to claim 1; and
a hair bleaching agent or oxidative hair dyeing agent comprising a first agent comprising an alkaline agent and a second agent comprising an oxidizing agent.

9. The hair bleaching or dyeing kit according to claim 8, wherein the hair cosmetic is suitable to be used before the hair bleaching agent or oxidative hair dyeing agent is applied to hair.

10. A method for pretreating hair for hair bleaching or oxidative hair dyeing with a hair bleaching agent or oxidative hair dyeing agent comprising a first agent comprising an alkaline agent and a second agent comprising an oxidizing agent, the method comprising:
applying the hair cosmetic according to claim 1 to hair.

11. A method for bleaching or dyeing hair, comprising:
applying a hair cosmetic to hair; and subsequently
applying a solution mixture of a first agent comprising an alkaline agent and a second agent comprising an oxidizing agent of a hair bleaching agent or an oxidative hair dyeing agent to the hair,
wherein said hair cosmetic, comprises:
(A) an aromatic sulfonic acid having a molecular weight of 300 or less or a salt thereof; and
(B) a cationic polymer having a cationic charge density of 4.5 meq/g or more,
wherein a mass ratio of the component (B) to the component (A), (B)/(A), is 0.7 or more and 5.0 or less.

12. A method for bleaching or dyeing hair, comprising:
applying a solution mixture of a hair cosmetic, a first agent comprising an alkaline agent, and a second agent comprising an oxidizing agent of a hair bleaching agent or an oxidative hair dying agent to hair,
wherein said hair cosmetic, comprises:
(A) an aromatic sulfonic acid having a molecular weight of 300 or less or a salt thereof; and
(B) a cationic polymer having a cationic charge density of 4.5 meq/g or more,
wherein a mass ratio of the component (B) to the component (A), (B)/(A), is 0.7 or more and 5.0 or less.

13. A method for bleaching or dyeing hair, comprising:
applying a solution mixture of a first agent comprising an alkaline agent and a second agent comprising an oxidizing agent of a hair bleaching agent or an oxidative hair dyeing agent to hair; and subsequently
applying a hair cosmetic to the hair,
wherein said hair cosmetic, comprises:
(A) an aromatic sulfonic acid having a molecular weight of 300 or less or a salt thereof; and
(B) a cationic polymer having a cationic charge density of 4.5 meq/g or more,
wherein a mass ratio of the component (B) to the component (A), (B)/(A), is 0.7 or more and 5.0 or less.

14. The method according to claim 10, wherein the mass ratio of the component (B) to component (A), (B)/(A), is 1.0 or more and 5.0 or less.

15. The method according to claim 10, wherein component (B) has a cationic charge density of 4.5 meq/g or more and 25 meq/g or less.

16. The method according to claim 10, wherein a content of the component (B) is 20 mass % or less.

17. The method according to claim 10, wherein said hair cosmetic further comprises:
(C) a compound represented by the formula (4) or a salt thereof:

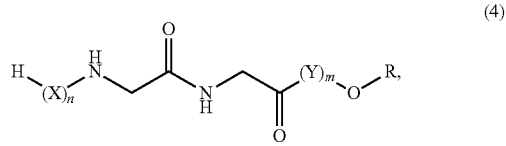

where X represents a divalent C1-C4 hydrocarbon group optionally substituted with a hydroxy group or an amino acid residue; Y represents an amino acid residue or a divalent group represented by the following chemical formula (5):

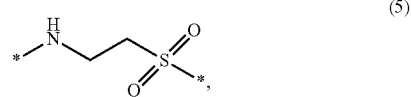

where -* represents a bond that binds to an adjacent carbonyl group or oxygen atom; R represents a hydrogen atom or a monovalent C1-C4 hydrocarbon group optionally substituted with a hydroxy group; and m and n each represent 0 or 1 provided that when in and n are both 1, X is not an amino acid residue.

18. The method according to claim 11, wherein the mass ratio of the component (B) to component (A), (B)/(A), is 1.0 or more and 5.0 or less.

19. The method according to claim 11, wherein component (B) has a cationic charge density of 4.5 meq/g or more and 25 meq/g or less.

20. The method according to claim 11, wherein a content of the component (B) is 20 mass % or less.

21. The method according to claim 11, wherein said hair cosmetic further comprises:
(C) a compound represented by the formula (4) or a salt thereof:

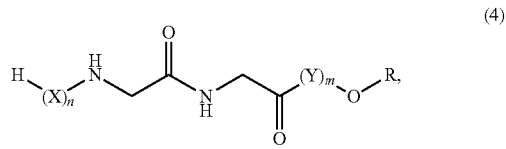

where X represents a divalent C1-C4 hydrocarbon group optionally substituted with a hydroxy group or an amino acid residue; Y represents an amino acid residue or a divalent group represented by the following chemical formula (5):

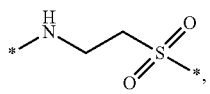

(5)

where -* represents a bond that binds to an adjacent carbonyl group or oxygen atom; R represents a hydrogen atom or a monovalent C1-C4 hydrocarbon group optionally substituted with a hydroxy group; and m and n each represent 0 or 1 provided that when in and n are both 1, X is not an amino acid residue.

22. The method according to claim 12, wherein the mass ratio of the component (B) to component (A), (B)/(A), is 1.0 or more and 5.0 or less.

23. The method according to claim 12, wherein component (B) has a cationic charge density of 4.5 meq/g or more and 25 meq/g or less.

24. The method according to claim 12, wherein a content of the component (B) is 20 mass % or less.

25. The method according to claim 12, wherein said hair cosmetic further comprises:
(C) a compound represented by the formula (4) or a salt thereof:

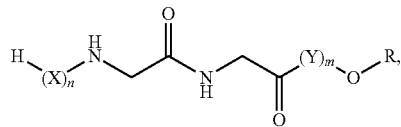

(4)

where X represents a divalent C1-C4 hydrocarbon group optionally substituted with a hydroxy group or an amino acid residue; Y represents an amino acid residue or a divalent group represented by the following chemical formula (5):

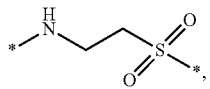

(5)

where -* represents a bond that binds to an adjacent carbonyl group or oxygen atom; R represents a hydrogen atom or a monovalent C1-C4 hydrocarbon group optionally substituted with a hydroxy group; and m and n each represent 0 or 1 provided that when in and n are both 1, X is not an amino acid residue.

26. The method according to claim 13, wherein the mass ratio of the component (B) to component (A), (B)/(A), is 1.0 or more and 5.0 or less.

27. The method according to claim 13, wherein component (B) has a cationic charge density of 4.5 meq/g or more and 25 meq/g or less.

28. The method according to claim 13, wherein a content of the component (B) is 20 mass % or less.

29. The method according to claim 13, wherein said hair cosmetic further comprises:
(C) a compound represented by the formula (4) or a salt thereof:

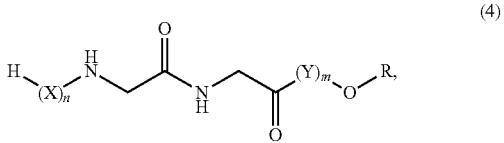

(4)

where X represents a divalent C1-C4 hydrocarbon group optionally substituted with a hydroxy group or an amino acid residue; Y represents an amino acid residue or a divalent group represented by the following chemical formula (5):

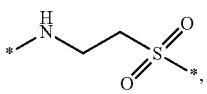

(5)

where -* represents a bond that binds to an adjacent carbonyl group or oxygen atom; R represents a hydrogen atom or a monovalent C1-C4 hydrocarbon group optionally substituted with a hydroxy group; and m and n each represent 0 or 1 provided that when m and n are both 1, X is not an amino acid residue.

30. The hair cosmetic according to claim 1, wherein said benzenesulfonic acid represented by formula (1) is one or more members selected from the group consisting of benzenesulfonic acid, o-toluenesulfonic acid, p-toluenesulfonic acid, xylenesulfonic acid, cumenesulfonic acid, ethylbenzenesulfonic acid, 2,4,6-trimethylbenzenesulfonic acid, and a salt thereof.

* * * * *

UNITED STATES PATENT AND TRADEMARK OFFICE
CERTIFICATE OF CORRECTION

PATENT NO. : 11,234,916 B2
APPLICATION NO. : 16/961808
DATED : February 1, 2022
INVENTOR(S) : Daisuke Hiruma et al.

It is certified that error appears in the above-identified patent and that said Letters Patent is hereby corrected as shown below:

In the Claims

In Column 26, Claim 14, Line 2, "(B) to component" should read -- (B) to the component --

In Column 26, Claim 15, Line 4, "wherein component" should read -- wherein the component --

In Column 26, Claim 18, Line 42, "(B) to component" should read -- (B) to the component --

In Column 26, Claim 19, Line 45, "wherein component" should read -- wherein the component --

In Column 27, Claim 22, Line 15, "(B) to component" should read -- (B) to the component --

In Column 27, Claim 23, Line 17, "wherein component" should read -- wherein the component --

In Column 28, Claim 26, Line 5, "(B) to component" should read -- (B) to the component --

In Column 28, Claim 27, Line 7, "wherein component" should read -- wherein the component --

Signed and Sealed this
Twenty-fourth Day of May, 2022

Katherine Kelly Vidal
*Director of the United States Patent and Trademark Office*